US00PP11596P

United States Patent [19]

Lemon

[11] Patent Number: Plant 11,596

[45] Date of Patent: Oct. 24, 2000

[54] REGAL PELARGONIUM PLANT NAMED 'IMPERIAL'

[75] Inventor: David G. Lemon, Lompoc, Calif.

[73] Assignee: Oglevee, Ltd., Connellsville, Pa.

[21] Appl. No.: 09/162,676

[22] Filed: Sep. 29, 1998

[51] Int. Cl.[7] ..... A01H 5/00

[52] U.S. Cl. ..... Plt./331

[58] Field of Search ..... Plt./331

[56] References Cited

U.S. PATENT DOCUMENTS

P.P. 8,909 9/1994 Walters ..... Plt./331

P.P. 9,893 5/1997 Walters ..... Plt./331

*Primary Examiner*—Howard J. Locker

*Assistant Examiner*—Wendy A Baker

*Attorney, Agent, or Firm*—Webb Ziesenheim Logsdon Orkin & Hanson, P.C.

[57] ABSTRACT

A new and distinct regal geranium plant with deep purple petals having white edges above a medium green foliage. The new variety has a larger growth habit with more vegetative shoots than 'Baron'.

1 Drawing Sheet

BACKGROUND OF THE INVENTION

This discovery relates to a new and distinct variety of geranium plant identified by the varietal name of 'Imperial', Breeder No. 4DG692 and Oglevee, Ltd. No. 64. The new variety was discovered in a selected breeding program at Oglevee, Ltd. in Connellsville, Pa. The new variety is a selection from the crossing of a breeding variety, Oglevee, Ltd. No. 261 (unpatented), and the commercial variety 'Baron', U.S. Plant Pat. No 8,909. The new variety was first asexually reproduced by cuttings at Connellsville, Pa. on Aug. 14, 1995. It has been found to retain its distinctive characteristics through successive generations.

The new variety, when grown in a glass greenhouse in Connellsville, Pa. using full light, 60° F. night temperature, 68° F. day temperature and grown in a soilless media with constant fertilizer at 150–200 ppm nitrogen and potassium, has a response time from a rooted cutting to a flowering plant in a 6 inch pot of fourteen weeks. Rooted cuttings potted Oct. 15, 1997 flowered Feb. 9, 1998.

DESCRIPTION OF THE DRAWING

The accompanying photographic drawing illustrates the new variety, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readings on a plant grown in a 5 inch pot were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium×domesticum*

*Varietal.*—Regal geranium named 'Imperial'.

Form: Upright medium mound.

Height: 28.0–30.0 cm.

Growth: Medium plant habit with free basal branching.

Strength: Does not need artificial support.

*Rooting speed.*—Cuttings produce 3 to 5 roots visible to outside of artificial growing media in 14 to 16 days.

Foliage: Stalked leaf attachment.

Leaves:

*Size.*—7.5–9.0 cm across.

*Shape.*—Depressed ovate; truncate base.

*Margin.*—Serrately lobed.

*Texture.*—Slightly pubescent, leathery.

*Color.*—Top: Green Group 137A. Bottom: Green Group 138B. Zone: None.

*Ribs and veins.*—Venation: Palmate. Color: Yellow-Green Group 147C.

Petioles:

*Length.*—4.0–7.0 cm.

*Color.*—Yellow-Green Group 144A.

Stem:

*Color.*—Yellow-Green Group 144A.

*Internode length.*—4.0–5.0 cm.

THE BUD

Shape:

*Overall.*—Elliptical cluster when just showing color.

*Individual buds.*—Elliptical or oval when just showing color.

Size: 3.0–4.5 cm when just showing color.

Number of buds per cluster: 10–12.

INFLORESCENCE

Blooming habit: Continuous flowering; medium sized florets forming a full flower head; 10–12 florets per umbel.

Borne: Umbel, florets on pedicel, pedicel on peduncle; peduncles are 6.0–8.5 cm above foliage.

Closed florets:

*Bud size.*—1.5–2.5 cm.

Open florets:

*Form.*—Slightly cupped.

*Size of fully open bloom.*—Umbel: 5.0–6.0 cm. Florets: 2.5–3.5 cm.

*Color.*—Top: Base and outer edge are White Group 155D. Veins begin at base and radiate toward lower sides of petal and range in color from Red-Purple Group 71A to Red-Purple Group 71B and also Greyed-Purple Group 187A. Center of petal is darkest at Greyed-Purple Group 187A. Bottom: Base and outer edge are White Group 155D. Veins start at base and radiate toward sides, range in color from Red-Purple Group 71A to Red-Purple Group 71B. Petal is darkest at center with Greyed-Purple Group 187A with Red-Purple Group 71A, Red-Purple Group 71B, and Red-Purple Group 72B shading to the white edge.

*Petals.*—Five in number.

Texture and appearance: Satiny, smooth; appears from a distance as a flower of deep purple accented with a white edge above medium green foliage.

Petaloids: None observed.

Pedicel:

*Length.*—1.5–2.0 cm.

*Color.*—Yellow-Green Group 144B.

Peduncle:

*Length.*—5.5–7.0 cm.

*Color.*—Yellow-Green Group 144B.

Disease resistance: No unusual susceptibility to diseases of Pelargonium has been observed.

Lasting quality: Overall plant bloom lasts up to 12 to 14 days when brought into the home as a pot plant.

REPRODUCTIVE ORGANS

Stamens:

*Anthers.*—3–5 mm long.

*Filaments.*—15–18 mm long; white in color.

*Pollen color.*—Golden orange.

Pistils:

*Number.*—1.

*Length.*—1.0–1.5 cm.

*Stigma color.*—Red-Purple Group 72A.

*Style.*—13 mm long.

*Ovaries.*—Pale green in color; pubescent; superior; 5 mm long.

*Fruit.*—None observed.

GENERAL CHARACTERISTICS

Cutting production and rooting speed are equal to or better than 'Baron'. Plant habit is slightly larger and with more vegetative shoots. Blooming time and flower quantity are both greatly improved over 'Baron'. The new variety flowers in 8 weeks, whereas 'Baron' flowers in 12 weeks. 'Imperial' produces more buds per cluster (10 to 12) than does 'Baron' (6 to 8). The rich deep purple accented with the white edge is very striking. This variety has been trialed during 1995, 1996, 1997 and has proven to be consistent and reliable.

I claim:

1. A new and distinct variety of geranium plant named 'Imperial' as described and illustrated herein.

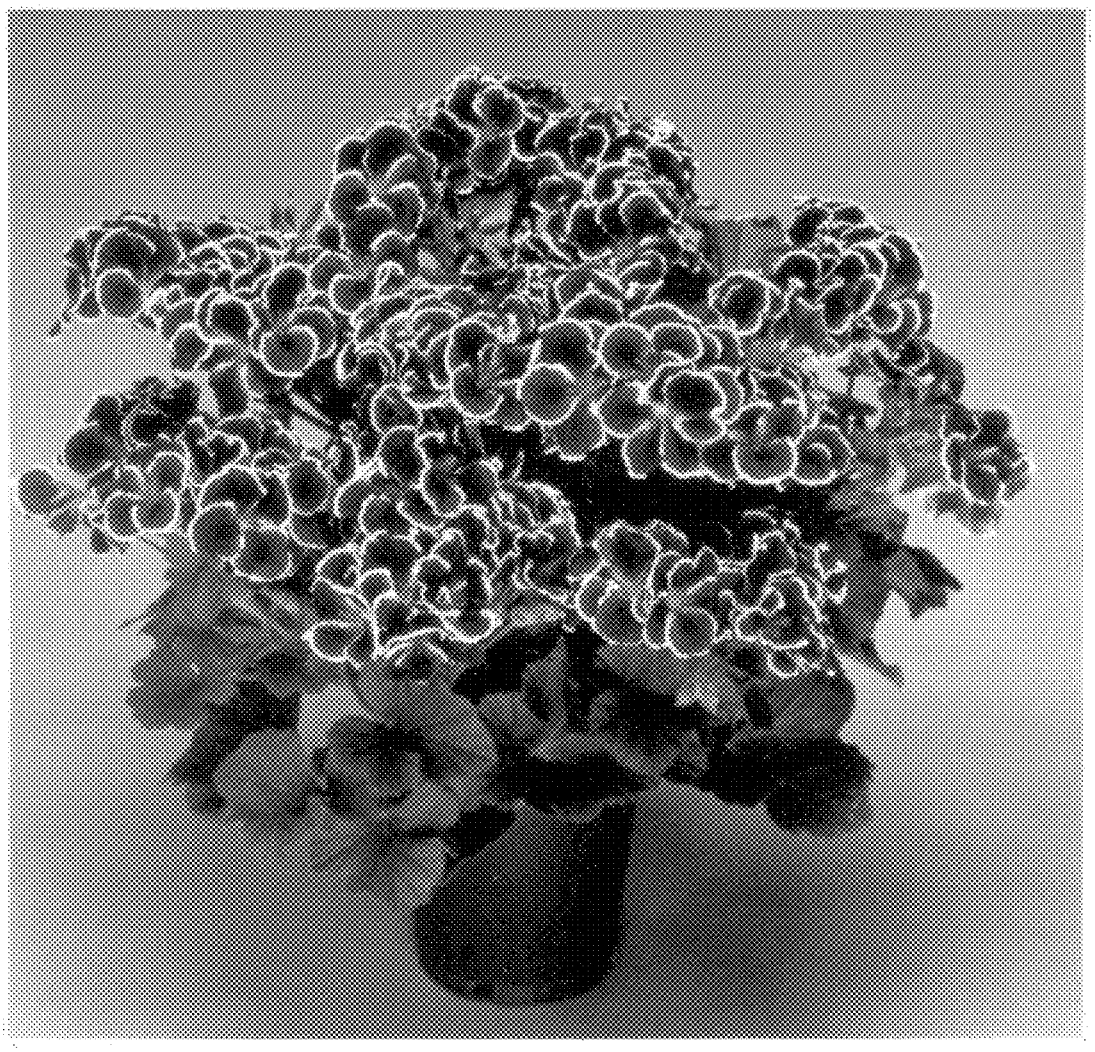

* * * * *